US009345887B2

(12) United States Patent
Sathaye et al.

(10) Patent No.: US 9,345,887 B2
(45) Date of Patent: *May 24, 2016

(54) LOCAL AND NON-LOCAL SENSING FOR CARDIAC PACING

(71) Applicant: Cardiac Pacemakers Inc., St. Paul, MN (US)

(72) Inventors: Alok Sathaye, Minneapolis, MN (US); Aaron R. McCabe, Edina, MN (US); Yinghong Yu, Shoreview, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 13/969,286

(22) Filed: Aug. 16, 2013

(65) Prior Publication Data

US 2014/0018878 A1 Jan. 16, 2014

Related U.S. Application Data

(63) Continuation-in-part of application No. 11/478,286, filed on Jun. 29, 2006, now Pat. No. 8,527,048.

(51) Int. Cl.
*A61N 1/368* (2006.01)
*A61N 1/365* (2006.01)
*A61B 5/0452* (2006.01)

(52) U.S. Cl.
CPC .............. *A61N 1/365* (2013.01); *A61B 5/0452* (2013.01); *A61N 1/3684* (2013.01); *A61N 1/36585* (2013.01); *A61N 1/3682* (2013.01)

(58) Field of Classification Search
CPC ........... A61N 1/36135; A61N 1/36139; A61N 1/3622; A61N 1/365; A61N 1/368; A61N 1/3682; A61N 1/3684
USPC ........................................... 607/4, 5, 9, 17, 25
See application file for complete search history.

(56) References Cited

U.S. PATENT DOCUMENTS

| 8,527,048 B2 | 9/2013 | Sathaye et al. |
| 2003/0004548 A1 * | 1/2003 | Warkentin ........................ 607/9 |

(Continued)

FOREIGN PATENT DOCUMENTS

WO WO-2008005270 A2 1/2008

OTHER PUBLICATIONS

"European Application Serial No. 07809967.8, Office Action mailed Feb. 17, 2009", 2 pgs.

(Continued)

*Primary Examiner* — Allen Porter, Jr.
(74) *Attorney, Agent, or Firm* — Schwegman Lundberg & Woessner, P.A.

(57) ABSTRACT

Systems and methods for determining pacing timing intervals based on the temporal relationship between the timing of local and non-local cardiac signal features are described. A device includes a plurality of implantable electrodes electrically coupled to the heart and configured to sense local and non-local cardiac signals. Sense circuitry coupled to first and second electrode pairs senses a local cardiac signal via a first electrode pair and a non-local cardiac signal via a second electrode pair. Detection circuitry is used to detect a feature of the local signal associated with activation of a heart chamber and to detect a feature of the non-local signal associated with activation of the heart chamber. A control processor times delivery of one or more pacing pulses based on a temporal relationship between timing of the local signal feature and timing of the non-local signal feature.

9 Claims, 10 Drawing Sheets

(56) References Cited

U.S. PATENT DOCUMENTS

2006/0047319 A1\* 3/2006 Bruhns et al. .................... 607/9
2008/0177344 A1\* 7/2008 Maskara et al. ................ 607/25
2012/0004697 A1\* 1/2012 Ternes et al. .................... 607/25

OTHER PUBLICATIONS

"European Application Serial No. 07809967.8, Response filed Mar. 17, 2009 to Office Action mailed Feb. 17, 2009", 15 pgs.

\* cited by examiner

LOCAL AND NON-LOCAL SENSING FOR CARDIAC PACING

RELATED APPLICATIONS

This application is a continuation-in-part of U.S. patent application Ser. No. 11/478,286, filed on Jun. 29, 2006, now U.S. Pat. No. 8,527,048 issued Sep. 13, 2013, which is hereby incorporated herein by reference.

FIELD OF THE INVENTION

The present invention relates generally to cardiac pacing therapy, and more specifically, to methods and systems for timing the delivery of pacing pulses based on local and non-local sensing of cardiac signals.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

Cardiac arrhythmia occurs when the heart rhythm is irregular or if the heart rate is too slow or too fast. During an arrhythmic episode, the heart's pumping action may become impaired and blood flow to peripheral tissues may be inadequate. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardia occurring in the atria of the heart, for example, includes atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias, as well as for patients with conditions such as congestive heart failure. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Some implantable cardiac rhythm management systems include one or more endocardial leads which may include electrodes for both pacing and defibrillation. Such implantable cardiac rhythm management (CRM) systems are capable of delivering low energy pacing pulses to the heart at intervals sufficient to support the body's hemodynamic requirements. The CRM system may also deliver high-energy defibrillation shocks to the heart.

Cardiac pacing therapy involves the use of pacing timing intervals between pacing pulses delivered to various heart chambers. Appropriate specification of these and other timing intervals is desired to achieve optimal improvement of cardiac function. For the reasons stated above, and for other reasons stated below which will become apparent to those skilled in the art upon reading the present specification, there is a need in the art for methods and systems that provide for determination of timing intervals for cardiac pacing therapy. The present invention fulfills these and other needs.

SUMMARY OF THE INVENTION

The present invention is directed to systems and methods for determining pacing timing intervals based on the temporal relationship between the timing of local and non-local cardiac signal features. One embodiment is directed to a method for delivery of pacing therapy. At least one local cardiac electrical signal and at least one non-local cardiac electrical signal are sensed using body-implantable electrodes. The method involves sensing for a feature of the local signal corresponding to activation of a heart chamber and sensing for a feature of the non-local signal corresponding to the activation of the heart chamber. Delivery of one or more pacing pulses is based on a temporal relationship between timing of the feature of the local signal and timing of the feature of the non-local signal.

Some implementations involve beat by beat determination of pacing timing intervals. In these implementations, sensing the local signal and sensing the non-local signal involves sensing these signals during a cardiac cycle. The delivery of pacing pulses for the cardiac cycle is based on a temporal relationship between the timing of features of the local signal and the non-local signal.

According to one aspect of the invention, timing the delivery of the pacing pulses involves determining an atrioventricular delay based on the temporal relationship between the local feature timing and the non-local feature timing. In one implementation, the local cardiac signal is sensed from a local atrial site. A local P-wave is detected from the local signal and a non-local P-wave is detected from the non-local signal. The delivery of the pacing pulses is timed based on the temporal relationship between the local P-wave and the non-local P-wave.

In another implementation, the local cardiac signal is sensed from a local atrial site. A local P-wave is detected from the local signal and a non-local P-wave is detected from the non-local signal. Timing delivery of the pacing pulses involves initiating the atrioventricular delay based on the detection of the local P-wave and ending the atrioventricular delay based on the detection of the non-local P-wave.

Various implementations of the invention involve delivery of trigger pacing. Pacing may be triggered to a single heart chamber or to contralateral heart chambers. For example, delivery of a pacing pulse may be triggered based on the timing of the non-local feature if the non-local feature is detected. If the non-local feature is not detected, the pacing pulse may be triggered based on the timing of the local feature. More specifically for atrial pacing, pacing may be triggered to one or more atria based on the timing of a non-local P-wave if the non-local P-wave is detected. If the non-local P-wave is not detected, pacing may be triggered based on the timing of a local P-wave. For ventricular pacing, pacing may be triggered to one or more ventricles based on the timing of a non-local QRS complex if the non-local QRS complex is detected. If the non-local QRS complex is not detected, pacing may be triggered based on the timing of a local QRS complex.

Another embodiment of the invention is directed to an implantable cardiac rhythm management device. The implantable device includes a plurality of implantable electrodes electrically coupled to the heart. At least a first pair of the plurality of electrodes is configured to sense a local cardiac signal. At least a second pair of the plurality of electrodes is configured to sense a non-local cardiac signal. Sense circuitry is coupled to the first and second electrode pairs and is configured to sense a local cardiac signal via the first electrode pair and a non-local cardiac signal via the second electrode pair. Detection circuitry is configured to detect a feature of the local signal associated with activation of a heart chamber and to detect a feature of the non-local signal associated with activation of the heart chamber. A control processor times delivery of one or more pacing pulses based on a temporal relationship between timing of the local signal feature and timing of the non-local signal feature.

For example at least one electrode of the second pair of electrodes may comprise a ring electrode, a defibrillation coil, or a subcutaneous, non-intrathoracic electrode.

According to one aspect of the invention, the local signal feature comprises a local P-wave and the non-local signal feature comprises a non-local P-wave. The control processor is configured determine an atrioventricular delay based on the temporal relationship between the timing of the local P-wave and the timing of the non-local P-wave. The atrioventricular delay is used to time delivery of the one or more pacing pulses. According to various aspects, the control processor may be configured to determine the atrioventricular delay based on the temporal relationship between a beginning, end, or peak timing of the local P-wave and a beginning, end, or peak timing of the non-local P-wave.

According to one aspect of the invention, the control processor is configured to trigger pacing based on the timing of the non-local signal feature if the non-local signal feature is detected and to trigger pacing based on the timing of the local signal feature if the non-local signal feature is not detected.

The pacing pulses may be delivered as part of a bradycardia pacing therapy, an atrioventricular pacing therapy and/or a resynchronization pacing therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
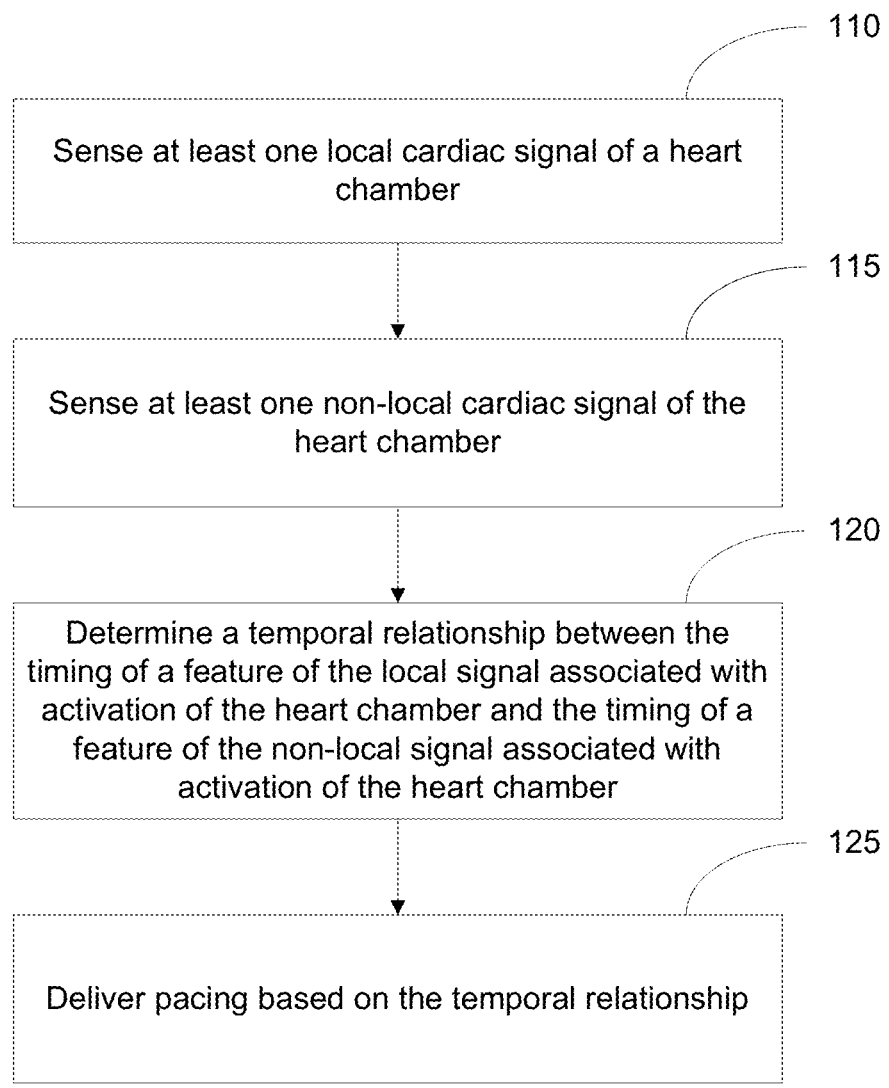
FIG. 1A is a flow diagram illustrating a method of determining pacing timing in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Mechanical contractions in the heart are triggered by waves of electrical depolarization that travel through the cardiac tissue. In a healthy heart, a depolarization wave for each cardiac cycle is initiated at the sinoatrial node and travels through specialized fibers to the heart chambers to cause synchronized contractions of the heart chambers. Due to disease, damage from myocardial infarction, and/or other degradation, the pathways and/or tissues involved in conduction of the depolarization wavefront may become compromised.

Pacemakers deliver electrical pacing pulses to the heart to produce contractions of the heart chambers in synchrony and at a rate sufficient to meet metabolic demand. Pacing therapy involves the implementation of timing intervals between various events during a cardiac cycle. The timing intervals may be used to control the rate of heart chamber contractions and/or the synchrony between heart chamber contractions. For example, for patients whose intrinsic heart rate is too slow, pacing assists the heart in contracting at a rate that is sufficient to provide blood flow to meet the patient's metabolic requirements. For patients suffering from congestive heart failure (CHF), cardiac pacing may be used to ensure that the contractions of the heart chambers occur in a timed sequence that improves heart function.

Pacemakers typically include cardiac electrodes that are in electrical contact with the myocardium and sense local cardiac electrical signals. The electrodes are used to sense cardiac electrical signals, such as cardiac signals associated with intrinsic or evoked cardiac depolarization events. Pacemakers that stimulate the heart according to timing intervals based on sensed cardiac events are capable of producing cardiac cycles that more closely mimic the physiological operation of a normal heart.

A cardiac electrical signal provides information about the depolarization status of the heart. Local sensing of cardiac signals may be achieved via electrodes that make contact with the cardiac myocardium. Local sensing using an electrode in contact with the myocardial tissue yields signals that are most strongly representative of the activation signals that are present close to the site of the electrode. Non-local sensing of the cardiac signals may be achieved via electrodes that are electrically coupled to, but do not make directed contact with, the myocardium. A sensed non-local cardiac activation signal is effectively a superposition of a number of activation signals occurring within the heart that are associated with a cardiac contraction.

In implantable pacemakers, tip electrodes which are configured to make direct contact with the myocardium, have traditionally been used for local sensing. Non-local sensing may be accomplished via various electrode pairs of an implantable pacemaker or defibrillator, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). For example, electrode pairs suitable for non-local sensing include RV-ring to RV-coil, RV-ring to SVC-coil, RV-ring to RA-ring, or may include sensing between two can electrodes, between a can electrode and an indifferent electrode, or between a can or indifferent electrode and a ring or coil electrode. An electrode pair, as used herein, refers to at least two electrodes, wherein each electrode of the pair may comprise multiple electrodes and/or multiple electrode elements used for sensing.

In some situations, the particular placement of a ring, coil, or other electrode configured for non-local sensing may cause the electrode to make direct contact with the myocardium. In these situations, unintentional local sensing is apparent from the cardiac waveform morphology and use of the electrode in conjunction with pacing parameter determination via non-local sensing in accordance with embodiments of the present invention may be avoided.

Embodiments of the invention are directed to systems and methods for timing the delivery of one or more pacing pulses based on sensed signals from local and non-local cardiac sites. The flow diagram of FIG. 1A illustrates a method of determining pacing timing in accordance with embodiments of the invention. At least one local cardiac signal is sensed 110 from at least one local cardiac site. At least one non-local cardiac signal is sensed 115 from at least one non-local site. A temporal relationship is determined 120 between the timing of a feature of the local signal associated with activation of a heart chamber and the timing of a feature of the non-local signal associated with activation of the heart chamber. Pacing is delivered 125 based on the temporal relationship.

Figure 1B:
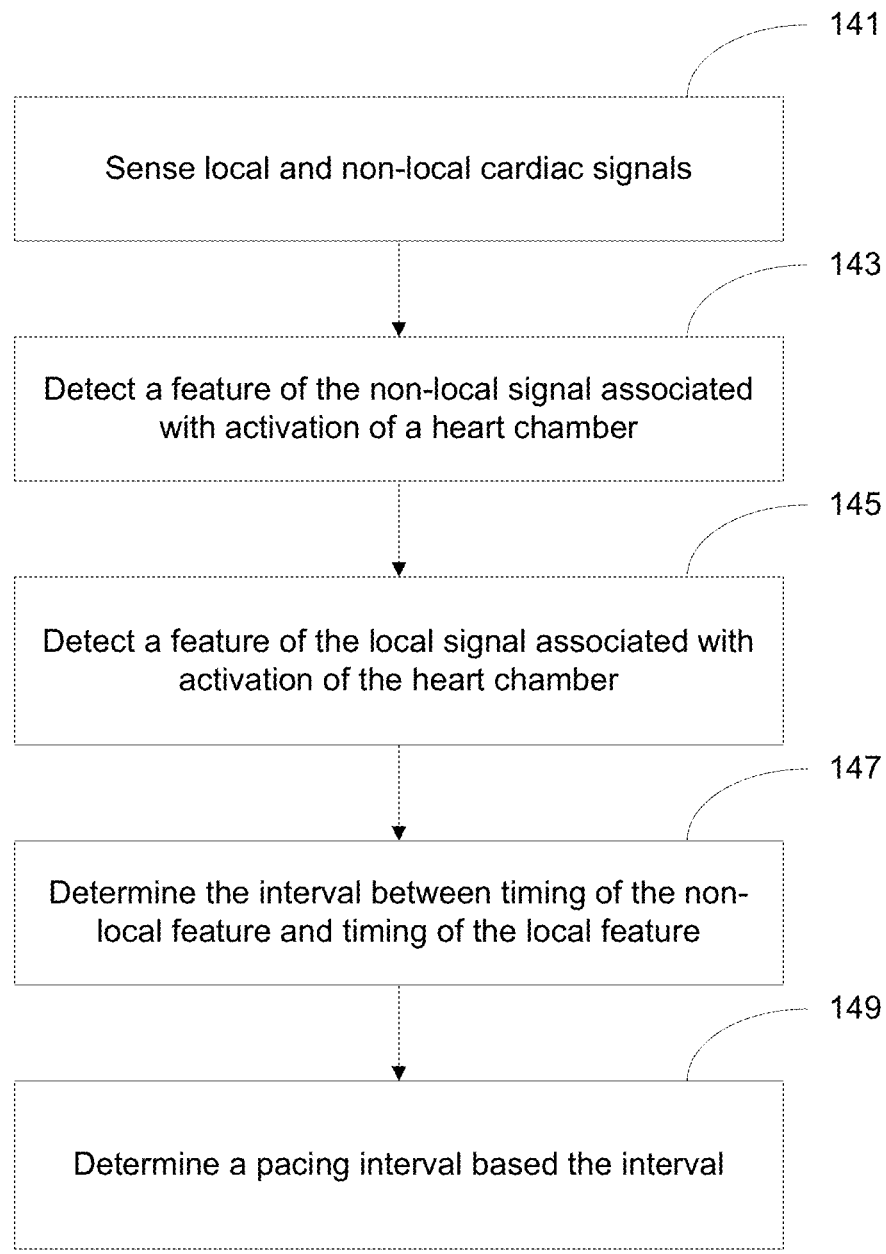
FIG. 1B is a flow diagram illustrating a method for determination of a pacing timing interval based on the interval between features of the local and non-local signals in accordance with embodiments of the invention.

According to some implementations, the local signal feature and the non-local signal feature are detected and the temporal relationship is determined as the interval of time between the local and non-local features. The flow diagram of FIG. 1B illustrates a method for determining a pacing interval, such as an atrioventricular delay, based on the time interval between features of the local and non-local signals in accordance with various embodiments. Local and non-local cardiac signals are sensed 141. A feature of the non-local signal associated with activation of a heart chamber is detected 143. A feature of the local signal associated with activation of the heart chamber is detected 145. The interval between the timing of the non-local signal feature and the timing of the detected local signal feature is determined 147. A pacing interval is determined 149 based on the interval between the non-local and local signal features.

In some implementations, both local and non-local signals are sensed and pacing is triggered based on detection of either a non-local signal feature or a local signal feature. For example, detection of a non-local feature may trigger pacing to one or more heart chambers. A feature of the local signal, which may be more reliably detected than the non-local feature, may be used to trigger pacing in the absence of detection of the non-local signal feature. In one example, sensing of both local and non-local signals is employed, but a feature of only one of the cardiac signals is detected and used to trigger the pacing.

Figure 1C:
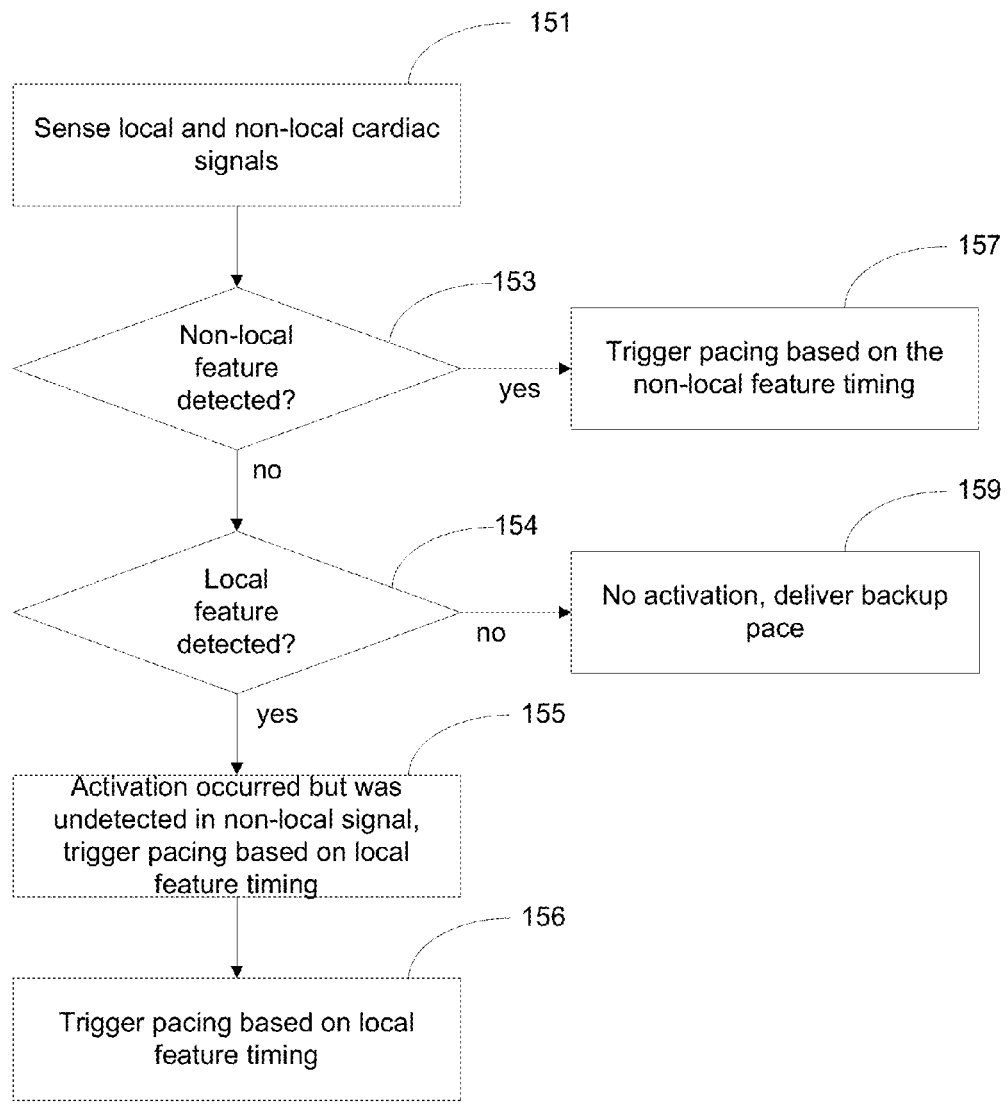
FIG. 1C is a flow diagram illustrating trigger pacing based on local and non-local signals in accordance with embodiments of the invention.

An embodiment directed to trigger pacing that relies on sensing both local and non-local signals is illustrated in the flow diagram of FIG. 1C. Both local and non-local signals are sensed 151. Detection 153 of a non-local signal feature associated with activation of a heart chamber triggers 157 delivery of a pacing pulse. In this embodiment, the non-local signal feature which is associated with activation of a heart chamber occurs prior to the local signal feature associated with activation of the heart chamber. If a non-local feature is not detected 153 and a local feature is detected 154, the system determines that activation has occurred, but the non-local feature was not detected 155. Pacing is triggered 156 based on the detected local signal feature. If no activation is detected from either the local or non-local signals, a backup pace may be delivered 159.

In various implementations, the delivery of one or more pacing pulses may be timed based on a pacing timing interval such as an atrioventricular timing interval, an interatrial timing interval and/or an interventricular timing interval. An atrioventricular pacing delay is a timing interval between an atrial sensed or paced event and delivery of a ventricular pace. The atrial event may be a right atrial event or a left atrial event and the ventricular pace may be a right ventricular pace or a left ventricular pace. An interatrial pacing delay is a timing interval between a sensed or paced event in one atrium and a pace delivered to the other atrium. An interventricular pacing delay is a timing interval between a sensed or paced event in one ventricle and a pace delivered to the other ventricle. Pacing pulses may be delivered to each of the electrodes in a timed sequence according to interchamber pacing delays that improve the contractile function. Timing the delivery of pacing pulses based on non-local sensing is particularly advantageous for cardiac resynchronization therapy because non-local sensing provides information about left chamber (e.g., left atrial) contractions without the need for local placement of left chamber sense electrodes.

Figure 2A:
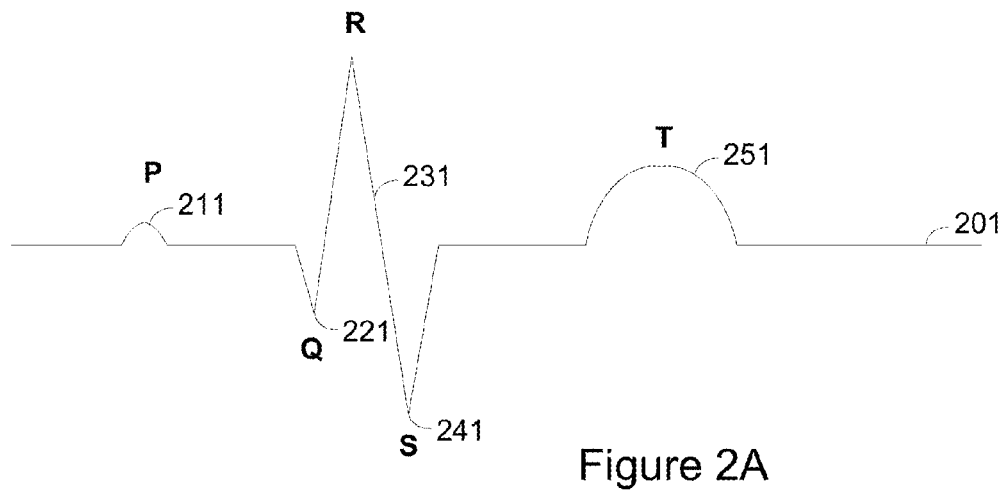
FIGS. 2A-2B illustrate local and non-local cardiac signals which may be used for timing the delivery of pacing pulses in accordance with embodiments of the invention.
Figure 2B:
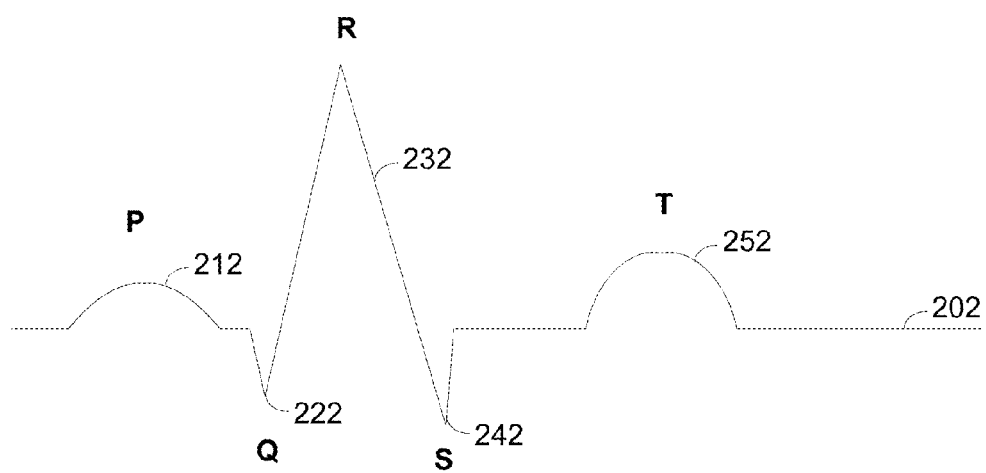

FIGS. 2A-2B illustrate local and non-local cardiac signals which may be used for timing the delivery of pacing pulses. FIGS. 2A and 2B illustrate cardiac signals 201, 202 sensed from a local site and a non-local site, respectively. In some implementations the local 201 and non-local 202 signals are sensed simultaneously. The portion of the cardiac signals 201, 202 representing activation of the atrial muscle fibers is referred to as a P-wave 211, 212. Activation of the ventricular muscle fibers is collectively represented by Q 221, 222, R 231, 232, and S 241, 242 waves of the cardiac signals 201, 202. The Q 221, 222, R 231, 232, and S 241, 242 waves are typically referred to collectively as the QRS complex, which is a well-known morphologic feature of electrocardiograms. Finally, the portion of the signal representing repolarization of the ventricular muscle fibers is known as a T wave 251, 252. Between contractions, the cardiac signal returns to an isopotential level during the T-wave 251, 252.

The cardiac signal 201 illustrated in FIG. 2A is typical of a local signal sensed using an electrode in contact with the myocardium. The cardiac signal 202 illustrated in FIG. 2B is typical of a non-local cardiac electrical signal, which is effectively a superposition of a number of activation signals. The cardiac signal 202 may be obtained via a non-local electrode pair electrically coupled to, but not in direct contact with, the myocardium.

Non-local sensing is particularly useful, for example, because it provides information about activation of the left atrium. Cardiac pacemakers providing resynchronization therapy typically include one or more electrodes in the right atrium for local sensing of right atrial activation signals. An atrioventricular delay (AVD) is initiated upon sensing an intrinsic depolarization of the right atrium or a right atrial pace. One or both ventricles are paced following the AVD. In some current devices, the conduction time delay resulting from paced or sensed atrial beats is accounted for by setting a fixed AVD based on population statistics and initiated by local right atrial sensing. A fixed AVD based on local right atrial sensing alone may not be appropriately timed to take into account a particular patient's interatrial conduction time. Further, if the atrium is paced, the atrial pacing results in a non-physiologic activation sequence that may further prolong activation of the atrium. If the fixed AVD is inappropriately programmed, the hemodynamic synchronization between atrial and ventricular contractions is sub-optimal.

The non-local signal provides information about left atrial activation timing and may be used in conjunction with the local signal to determine an AVD tailored to a particular patient and/or tailored to a particular type of pacing cycle. A pacing cycle in which one or both atria are paced may use an AVD having a different duration than a pacing cycle in which the atria are not paced. As described herein, local and non-local sensing may be used to provide a dynamically adjustable AVD. In some implementations, the duration of the AVD may be determined based at least in part on the timing of the end of the non-local P-wave. In some implementations, the AVD may be determined based on the temporal relationship between the timing of the end of the local P-wave and the timing of a feature of the non-local P-wave.

Embodiments of the present invention provide pacing timing optimization approaches that are patient specific and allow dynamic adjustment of interchamber pacing delays. According to various embodiments, timing information associated with features of the local and non-local signals may be used to determine pacing timing delays. For example, timing intervals may be based on the relationship between feature points, such as the start, end, or peak value, of the local signal and feature points, such as the start, end, or peak value, of the non-local signal. The timing of the delivery of pacing pulses may be based on widths of various features. In one implementation, the length of the AVD, which determines the timing of the delivery of a ventricular pacing pulse, is related to the P-wave width of the non-local signal. The non-local P-wave width is representative of the conduction delay between the right and left atria. Generally, a relatively larger P-wave width indicates a longer conduction delay in the activation signals propagating between the atria. Using the non-local P-wave width in the determination of the AVD allows for synchronous atrioventricular pacing so that pacing pulses are delivered to one or both ventricles at an optimal time following the atrial contraction. Improved timing of ventricular pacing improves cardiac pumping action and increases output.

In some configurations, adjustment of the pacing timing intervals may be performed for each cardiac cycle on a beat by beat basis. In some configurations, one or more pacing timing intervals may be determined using data collected from local and non-local signals of previous cardiac cycles.

Figure 3:
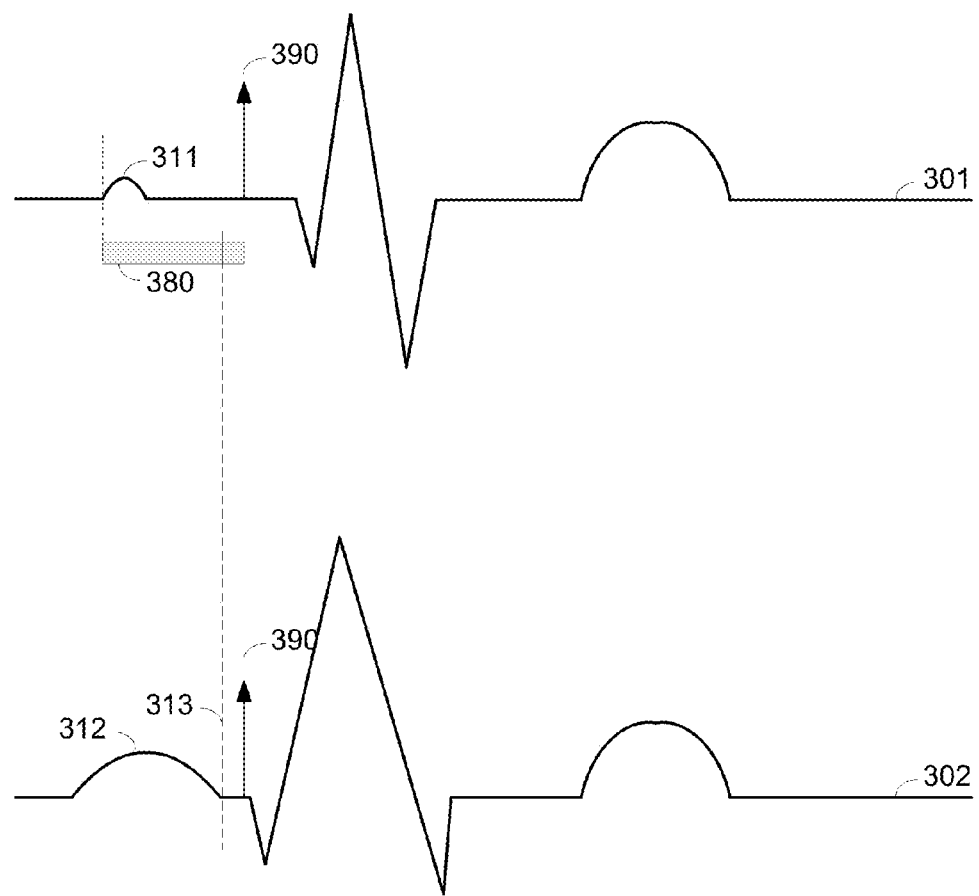
FIG. 3 shows graphs of local and non-local signals illustrating the determination of an atrioventricular delay (AVD) in accordance with embodiments of the invention.
Figure 4:
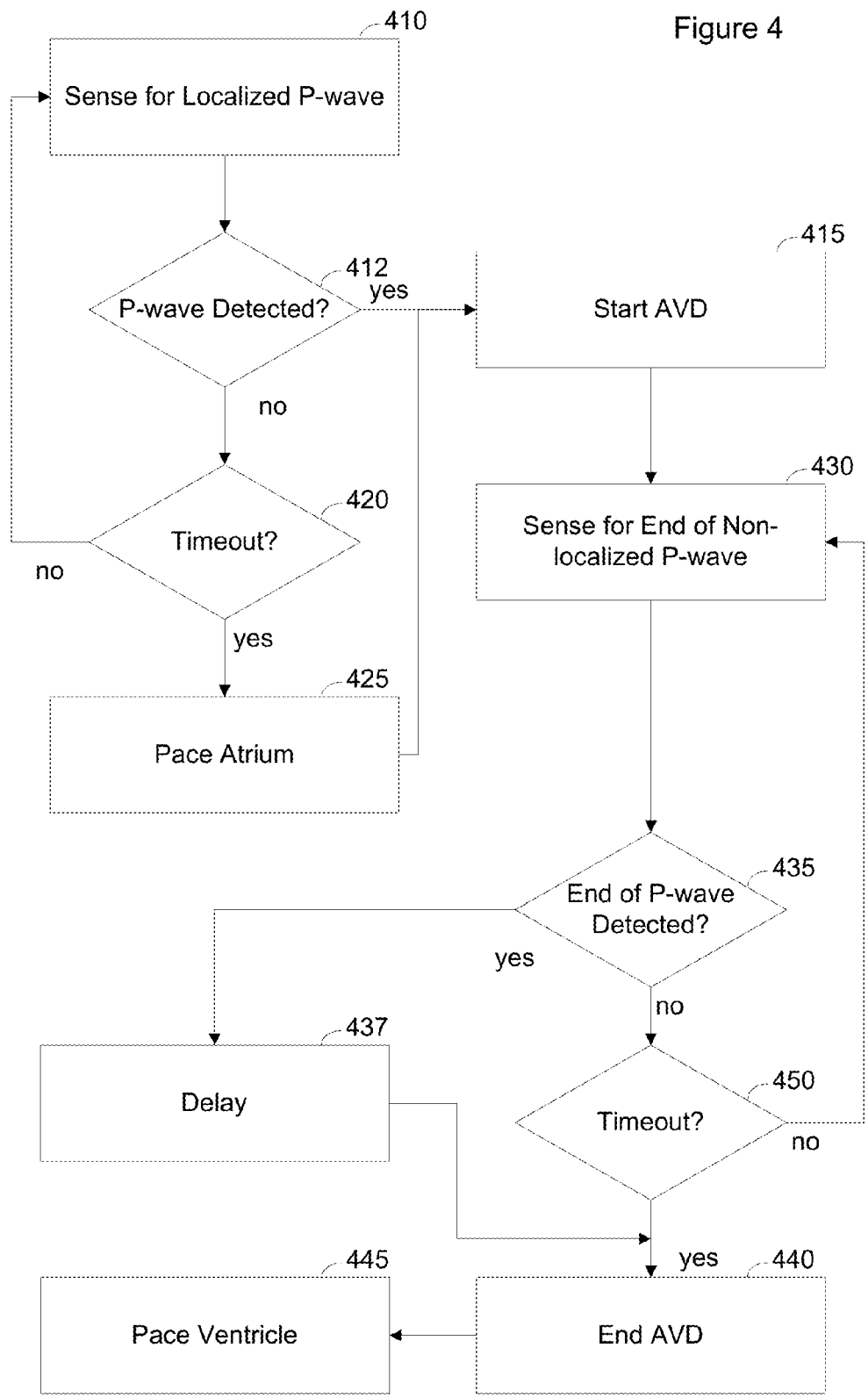
FIG. 4 is a flow diagram illustrating a method for beat by beat adjustment of AVD based on P-waves detected from local and non-local signals of each cardiac cycle in accordance with embodiments of the invention.

One example, illustrated by the graph of FIG. 3 and the flow diagram of FIG. 4, involves the beat by beat adjustment of AVD based on P-waves detected from both the local 301 and non-local 302 signals of each cardiac cycle. The device senses for a P-wave 311 on the local signal 301 and initiates an AVD 380 if the local P-wave 311 is detected. The device detects the end 313 of the non-local P-wave 312. Following a predetermined interval from the end 313 of the non-local P-wave 312, the AVD 380 ends and a pacing pulse 390 is delivered to a ventricle. In some embodiments, the AVD 380 is dynamically adjusted beat by beat using the process described above based on the detection of the local P-wave 311 and the timing of the end 313 of the non-local P-wave 312.

Beat by beat adjustment of the AVD based on local and non-local P-waves is further illustrated by the flowchart of FIG. 4A. The device senses for 410 a P-wave on the local signal. If the local P-wave is detected 412, then the AVD delay is started 415. If a timeout interval is exceeded 420 while sensing for the local P-wave, then the atrium is paced 425.

The device senses 430 for the end of a non-local P-wave. If the non-local P-wave is detected 435, then the AV delay ends 440 after a predetermined time delay 437 and a pacing pulse is delivered 445 to one or both ventricles. The predetermined time delay may be zero or may be greater than zero and less than about 300 msec, for example. Selection of the predetermined time delay may be based on clinical data or on individualized data from the patient, such as interchamber conduction data. Particularly for CHF patients, the predetermined time delay may be selected to produce optimal cardiac pumping function and/or reduce the symptoms of CHF. The predetermined time delay may be adjustable based on acute or chronic factors, such as the patient's metabolic demand or disease progression.

If, while waiting for the end of the non-local P-wave, a timeout interval is exceeded 450, then the AVD ends 440 and a pacing pulse is delivered 445 to one or both ventricles.

Figure 5:
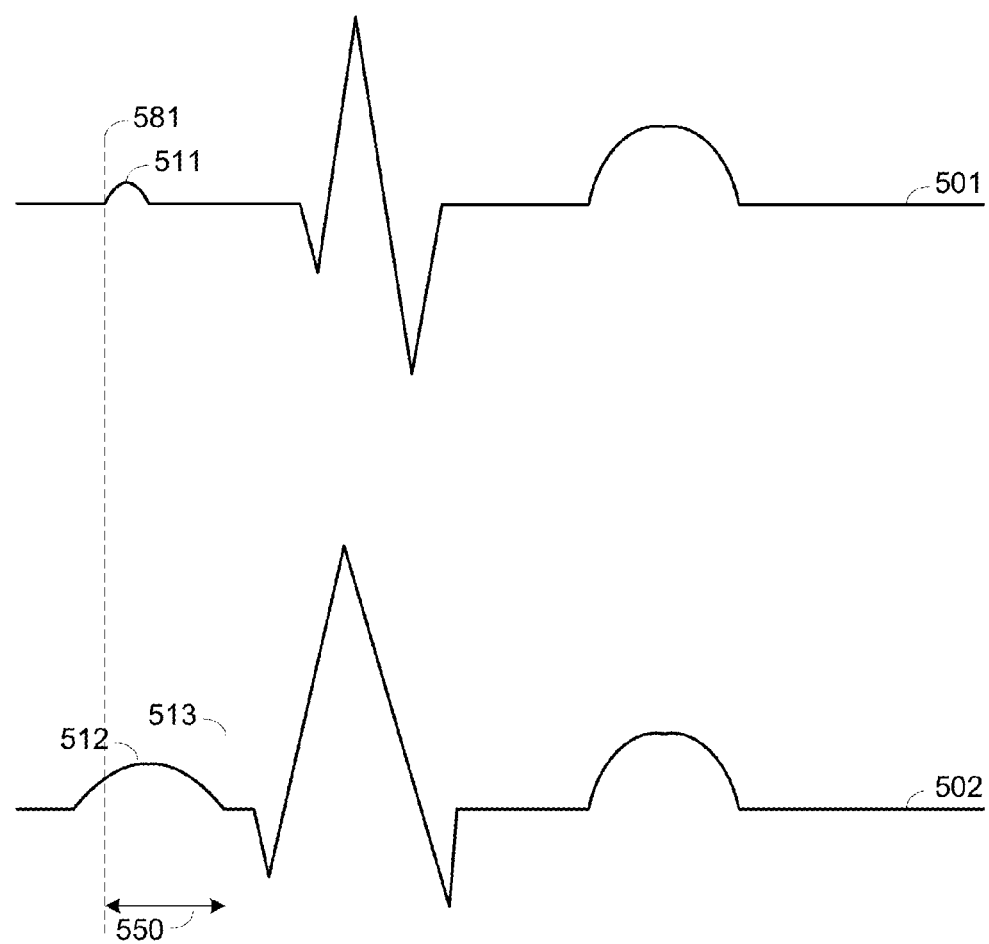
FIG. 5 is a graph illustrating determination of AVD for a cardiac cycle based on the local and non-local signal features of one or more previous cardiac cycles in accordance with embodiments of the invention.

The graph of FIG. 5 illustrates a method for determining the AVD according to another embodiment. In this embodiment, local 501 and non-local 502 signals are sensed for one or more cardiac cycles. The system searches for a feature point 581 of the local P-wave 511, such as the start, end, or peak of the local P-wave. In the example illustrated in FIG. 5, the system searches for the beginning 581 of the local P-wave. The system searches a feature point of the non-local P-wave 512, such as the end 513 of the non-local P-wave 512. The interval 550 between the beginning 581 of the local P-wave 511 and the end 513 of the non-local P-wave 512 is measured for one or multiple cardiac cycles. The AVD is determined based on the measured intervals 550. For example, the AVD may be determined based on a median, mean, or weighted average of the measured intervals. The device uses the AVD for subsequent cardiac cycles. Periodically, the AVD may be updated using the process described above.

In some embodiments, a number of AVDs may be determined as described in FIG. 5 for different heart rates. The AVDs may be indexed by rate and stored. If a particular heart rate is detected, an AVD corresponding to the particular rate may be selected for use. Different AVDs may be determined for intrinsic and paced beats. Use of both the local and non-local signals for determination of the AVD as described herein produces pacing that is consistent for intrinsic and paced beats. The determination of AVD based on non-local sensing provides the ability to react to cases in which the atrial lead position results in shorted paced P-waves, as has been shown in lower atrial septal pacing.

In some embodiments, timing the delivery of pacing pulses involves triggering pacing of a heart chamber or contralateral heart chambers based on one or more signal features. This implementation is particularly useful for triggered ventricular pacing in patients having prolonged interatrial conduction times and ventricular conduction abnormalities. In these patients, activation of the ventricles may precede sensed activation at the local ventricular sense electrode. As described more fully below, the non-local signal may be used to detect the first activation of the ventricles. Biventricular pacing may be triggered based on the first ventricular activation detected via the non-local signal. Biventricular trigger pacing as provided by this embodiment uses intrinsic conduction to activate the septum and promote fusion between intrinsically conducted activation and paced ventricular activity to achieve optimized cardiac performance for individual patients.

Figure 6:
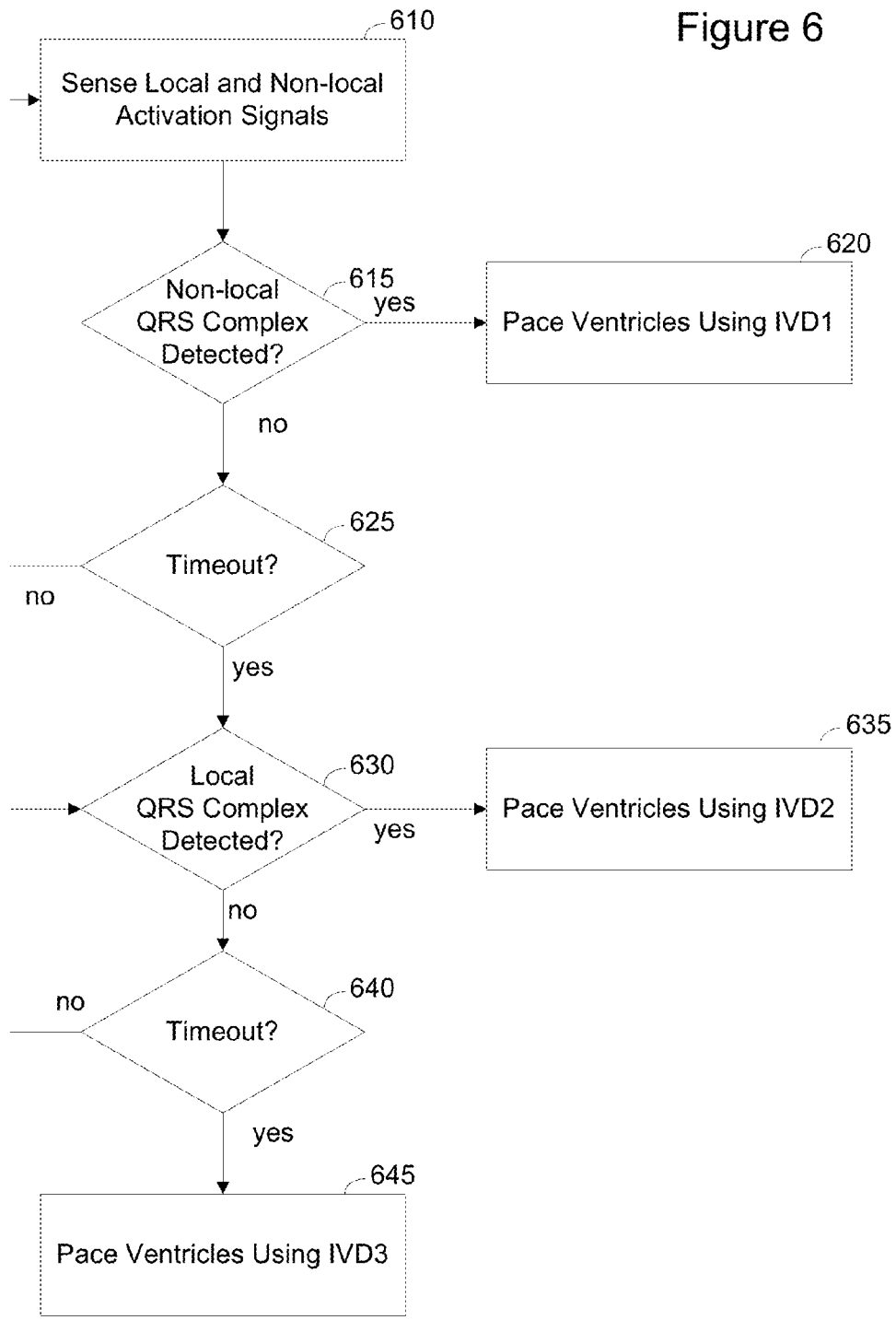
FIG. 6 is a flow diagram of a method for implementing triggered pacing with backup pacing in accordance with an embodiment of the invention.

The flowchart of FIG. 6 illustrates ventricular pacing triggered by a feature point of the non-local signal with backup pacing implemented using a pacing timing delay initiated by a local signal. Although the example of FIG. 6 is directed to triggered ventricular pacing, a similar process may be implemented for triggered atrial pacing. The device senses 610 signals from a local ventricular site and a non-local site. If the initiation of a QRS complex is detected 615 on the non-local signal, pacing is triggered 620 to one or both ventricles. The ventricles are paced using a first interventricular delay IVD1. If the initiation of the QRS complex is not detected 615, and a timeout has occurred 625, then an alternate process for timing ventricular pacing is used. If the QRS complex has been detected 630 on the local right ventricular signal, then the left ventricle is paced 635 using IVD2. If the right ventricular QRS complex is not detected 640 following a timeout period, then the right and left ventricles are paced 645 using IVD3.

In some embodiments, IVD1, IVD2, and IVD3 may have the same duration. In other embodiments, one or more of the IVDs used in the above example may be selected to achieve optimal cardiac output for the particular pacing timing situation. The IVDs may be determined, for example, from previously detected local and/or non-local signals. The IVDs may be determined based on the QRS complex width of the non-local signal, or the interval between a local signal feature point and a non-local signal feature point, or by other methods.

A wide variety of implantable cardiac stimulation devices may be configured to sense local and non-local signals and time the delivery of pacing pulses in accordance with the present invention. A non-limiting, representative list of such devices includes pacemakers, cardiovertors, defibrillators, resynchronizers, and other cardiac therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). A cardiac therapy device implemented in accordance with the present invention may incorporate one or more of the electrode types identified above and/or combinations thereof to sense local and non-local signals.

Figure 7:
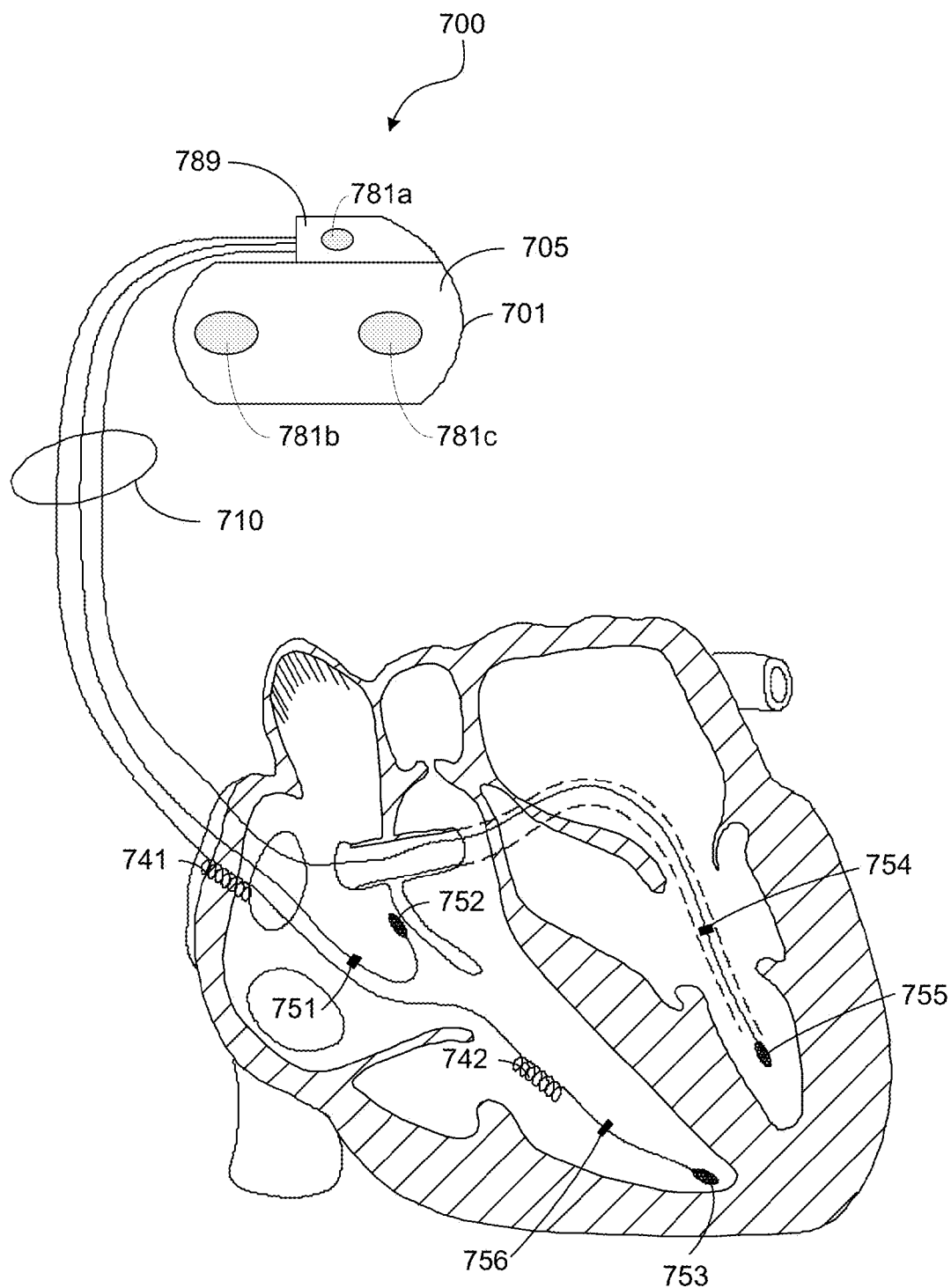
FIG. 7 illustrates a therapy device that may be used to time the delivery of cardiac pacing pulses based on local and non-local sensing in accordance with embodiments of the invention.

Referring now to FIG. 7, the implantable device illustrated in FIG. 7 is an embodiment of a therapy device 700 that may be used to time the delivery of cardiac pacing pulses based on local and non-local sensing in accordance with embodiments of the invention. In this example, the therapy device 700 includes a pulse generator 705 electrically and physically coupled to an intracardiac lead system 710.

Portions of the intracardiac lead system 710 are inserted into the patient's heart. The intracardiac lead system 710 includes one or more electrodes configured to sense electrical cardiac activity of the heart and deliver electrical stimulation to the heart. Additionally, the cardiac electrodes and/or other sensors may be used to sense the patient's transthoracic impedance, and/or sense other physiological parameters, such as cardiac chamber pressure or temperature. The electrodes shown in FIG. 7 illustrate one possible arrangement of electrodes. Many other electrode arrangements, including intracardiac and/or subcutaneous intrathoracic and non-intrathoracic electrodes, may be used to achieve local and non-local sensing and are considered to fall within the scope of the invention. The lead system 710 may include wired and/or wirelessly coupled electrodes. In wireless configurations, sensed signals from the electrodes are wirelessly communicated to the pulse generator 705 and/or may also be communicated wirelessly to a patient-external device.

Portions of the housing 701 of the pulse generator 705 may optionally serve as one or multiple can or indifferent electrodes. The housing 701 is illustrated as incorporating a header 789 that may be configured to facilitate removable attachment between one or more leads and the housing 701. The housing 701 of the pulse generator 705 may include one or more can electrodes 781*b*, and 781*c*. The header 789 of the pulse generator 705 may include one or more indifferent electrodes 781*a*. The housing 701 and/or header 789 may include any number of electrodes positioned anywhere in or on the housing 701 and/or header 789. In various configurations, one or more housing/header electrodes 781*a*-781*c* may be used as one electrode of an electrode pair 781*a*-781*c* providing non-local sensing and another one or more housing/header electrodes 781*a*-781*c* may be used as the other electrode of the electrode pair. In other embodiments, one or more housing/header electrodes 781*a*-781*c* may be used as one electrode of a non-local electrode pair providing non-local sensing and one or more intracardiac electrodes such as the SVC coil 741, RA ring 751, RV coil 742, RV ring 756, and/or LV ring electrode 754 may be used as the other electrode of the non-local electrode pair. Local signals may be sensed via tip electrodes configured for local sensing such as the RA tip electrode 752, the RV tip electrode 753 and the LV distal electrode 755.

Communications circuitry is disposed within the housing 701 for facilitating communication between the pulse generator 705 and a patient-external device, such as an external programmer or advanced patient management (APM) system, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may include circuitry, such as filters, amplifiers, digitizers and/or other signal processing circuitry for useful in sensing local and non-local cardiac signals. The pulse generator may also include circuitry for detecting and/or measuring signal features. Control circuitry for controlling pacing and/or defibrillation/cardioversion therapy and other functions of the pacemaker is enclosed in the housing of the pulse generator 705.

The lead system 710 and pulse generator 705 of the therapy device 700 may incorporate one or more transthoracic impedance sensors that may be used to acquire the patient's respiratory waveform, and/or other respiratory-related information. The transthoracic impedance sensor may include, for example, one or more intracardiac electrodes 741, 742, 751-756 positioned in one or more chambers of the heart. The intracardiac electrodes 741, 742, 751-756 may be coupled to impedance drive/sense circuitry positioned within the housing 701 of the pulse generator 705. Information from the transthoracic impedance sensor and/or an activity sensor may be used to adapt the rate of pacing to correspond to the patient's activity and/or hemodynamic need.

The lead system 710 may include one or more cardiac pace/sense electrodes 751-756 positioned in, on, or about one or more heart chambers for sensing electrical signals from the patient's heart and/or delivering pacing pulses to the heart. The intracardiac sense/pace electrodes 751-756, such as those illustrated in FIG. 7, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The pulse generator 705 may include circuitry for detecting cardiac arrhythmias and/or for controlling pacing or defibrillation therapy in the form of electrical stimulation pulses or shocks delivered to the heart through the lead system 710.

In some embodiments, the pulse generator 705 may include circuitry for determining interchamber pacing timing intervals, such as AVD and/or IVD, using the local and non-local signals. In other embodiments, the pulse generator 705 may transfer sensed or derived information relevant to the determination of pacing timing to a patient-external device. Following download of the implantably sensed or derived information, determination of pacing timing intervals may be made by the patient-external device or may be made by a human analyst. Following pacing timing determination, the pacing timing intervals may be transferred to the therapy device 700 and used to control pacing pulses delivered to the heart to effect a pacing therapy for enhancing cardiac function.

Figure 8:
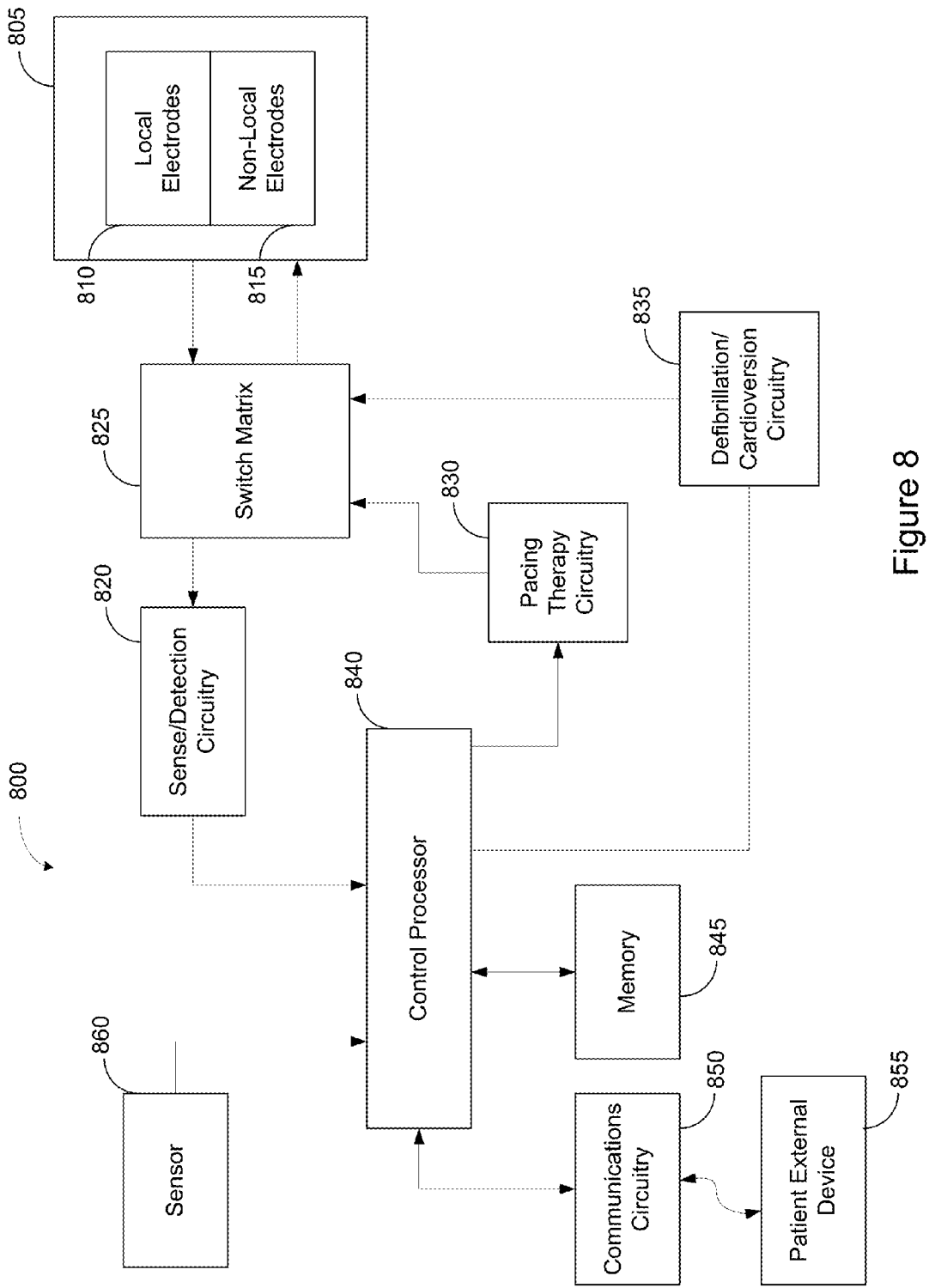
FIG. 8 is a block diagram depicting various components of a system that may be used to deliver pacing therapy with pacing timing implemented in accordance with embodiments of the invention.

FIG. 8 is a block diagram depicting various components of a system that may be used to deliver pacing therapy with pacing timing implemented in accordance with embodiments of the invention. The components, functionality, and configurations depicted are intended to provide an understanding of various features and combinations of features that may be incorporated in such a system. It is understood that a wide variety of device configurations are contemplated, ranging from relatively sophisticated to relatively simple designs. As such, particular configurations may include some components illustrated in FIG. 8, while excluding other components. In certain embodiments, the arrangement of the functional blocks may vary from the arrangement depicted.

FIG. 8 illustrates functionality for timing delivery of pacing pulses based on the use of local and non-local signals. In some embodiments, the functionality may be incorporated into an implantable device. In other embodiments, the functionality may be incorporated in the patient-external programmer. In yet other embodiments, the functionality may be divided between a patient implantable device and a patient external device.

In some implementations, the control processor 840 may execute a relatively sophisticated algorithm that automatically determines pacing the control processor may format information for display to allow a human analyst to review information from local and non-local signals to make a determination regarding optimal timing for pacing.

Illustrated in FIG. 8 is a therapy system 800 having control processor 840 coupled to appropriate memory (volatile and/or non-volatile) 845, it being understood that any logic-based control architecture may be used. The control processor 840 is also coupled to circuitry and components configured to sense electrical signals produced by the heart and to deliver electrical stimulation energy to the heart under predetermined conditions to treat cardiac arrhythmias and/or other cardiac conditions. The electrical energy delivered by the therapy device 800 may be in the form of low energy pacing pulses or high-energy pulses for cardioversion or defibrillation.

Cardiac signals are sensed using cardiac electrodes 805, including local 810 and non-local electrodes 815. A switch matrix 825 is employed to selectably couple various combinations of the cardiac electrodes 805 to the sensing circuitry 820. The sensed cardiac signals are received by sensing circuitry 820, which includes circuitry and for amplifying, filtering and/or digitizing the local and non-local signals. The sensed cardiac signals may optionally be processed by noise reduction circuitry (not shown), which may reduce noise and or increase the signal to noise ratio (SNR) of the signals before signals are sent to the control processor 840.

The control processor 840 may include arrhythmia detection circuitry such as a signal processor that coordinates analysis of the sensed cardiac signals and/or other sensor inputs to detect cardiac tachyarrhythmia. Rate based and/or morphological discrimination algorithms may be implemented by the control processor 840 to detect and verify the presence and severity of an arrhythmic episode. If arrhythmia is detected, the therapy control processor 840 may coordinate delivery of an appropriate therapy, such as anti-tachyarrhythmia pacing therapy (ATP), cardioversion, and/or defibrillation via the defibrillation/cardioversion circuitry 835 to terminate or mitigate the arrhythmia.

The therapy device 800 incorporates cardiac pacing capability in addition to, or to the exclusion of, cardioversion and/or defibrillation capabilities. As is shown in FIG. 8, the therapy device 800 includes pacing therapy circuitry 830 that is coupled to the therapy control processor 840 and to the electrodes 805 via the switch matrix 825. Under the control of control processor 840, the pacing therapy circuitry 830 delivers pacing pulses to the heart in accordance with a selected pacing therapy, such as a pacing therapy using pacing timing intervals determined by the approaches described herein.

Control signals, developed in accordance with a pacing regimen by pacemaker circuitry within the therapy control processor 840, are initiated and transmitted to the pacing therapy circuitry 830 where pacing pulses are generated. A pacing therapy, such as those discussed and incorporated herein, may be modified by the therapy control processor 840. Pacing therapy may be implemented to terminate or mitigate cardiac tachyarrhythmia, to provide a heart rate that ensures sufficient blood flow, and/or to enhance synchronization of the heart chamber contractions.

The sensing circuitry 820 is configured to sense local and non-local cardiac electrical signals via the electrodes 810, 815 and to communicate cardiac signal information to the control processor 840. The control processor 840 may also be configured to receive signals from one or more additional physiologic and/or non-physiologic sensors 860. The additional physiological signals and/or non-physiological signals may be used in connection with various diagnostic, therapeutic or monitoring implementations. For example, the therapy device 800 may include sensors or circuitry for detecting respiratory system signals, cardiac system signals, and/or signals related to patient activity or metabolic demand. The therapy control processor 840 may adapt the pacing rate based on the patient's sensed metabolic demand.

Cardiac signals sensed via the local and/or non-local electrode pairs 810, 815 are used by the control processor 840 to determine timing for pacing pulses as described herein. For example, the control processor 840 may analyze the sensed signals to detect signal features. The control processor 840 may determine interchamber timing delays, such as AVD and/or IVD, for pacing therapy based on the signal features. The control processor 840 may implement trigger pacing and may deliver backup pacing based on local and non-local sensing.

Memory circuitry 845 of the therapy device 800 contains parameters for operating in various monitoring, defibrillation, and pacing modes. The memory circuitry 845 may also be configured to store historical data, which may be used for various purposes and transmitted to an external receiving device 855 as needed or desired. For example, in certain embodiments, the memory circuitry 845 may store formulas and/or tables used in connection with determining pacing timing. The formulas and/or tables may be indexed according to heart rate.

Communications circuitry 850 is coupled to the control processor 840. The communications circuitry 850 allows communication between devices, such as patient-external devices 855 and patient-implantable devices. In one configuration, the communications circuitry 850 and the patient-external device 855 use a wire loop antenna and a radio frequency telemetric link, as is known in the art, to receive and transmit signals and data between the patient-external device 855 and communications circuitry 850. In this manner, programming commands and data may be transferred to the control processor 840 from the patient-external device 855 during and after implant. Using a patient-external programmer, a physician is able to set or modify various parameters used by the therapy control processor 850. For example, a physician may set or modify parameters affecting monitoring, detection, pacing, and defibrillation functions of the therapy control processor 840.

In certain embodiments, the control processor 840 transmits information for determination of pacing timing to the patient-external device 855. The information may include, for example, cardiac electrical signals obtained via local and/or non-local sensing, markers indicating the timing of certain features or points, measured characteristics or features of the signals, and/or other information. The patient-external device 855 may use the transmitted information to determine pacing timing intervals or may format and display information from local and non-local sensing to facilitate the determination of pacing timing intervals by a human analyst.

Processes for timing the delivery of pacing pulses based on cardiac signals obtained via local and non-local sensing in accordance with embodiments of the invention may be implemented by an implantable device, by a patient-external device, such as a programmer or advanced patient management system, or by a manually implementable procedure, such as by using a printed table lookup to compute the optimal values, and/or by any combination of these techniques.

In one embodiment, the patient-external programmer 855 communicates with the control processor 840 over a telemetry link and receives either raw electrogram data, markers corresponding to particular sensed events, and/or measurements of intervals between sensed events or feature widths as computed by the implantable device. The external programmer 855 may then compute optimal settings for pacing timing intervals which are either transmitted to the control processor 840 for immediate reprogramming or presented to a clinician operating the external programmer as recommendations.

In another embodiment, the external programmer 855 may present the data, markers, and/or measurements to a human analyst who then programs the control processor 840 in accordance with an algorithm. In yet a further embodiment, determination of the pacing timing may be fully automatic and performed by an implantable therapy device.

CRT patients who are paced using inappropriate pacing timing delays may not benefit by CRT therapy. One goal of CRT is to optimize the LA/LV timing in order to increase atrioventricular synchrony and thus enhance cardiac performance. The use of RA local signals to determine timing intervals is hindered by the lack of LA information available using RA local sensing alone. The difference in activation sequences between intrinsic and paced activity further complicates achieving optimal atrioventricular synchrony due to variable patient physiology and pathology. Non-local sensing of signals provides additional information useful for determining pacing timing that promotes atrioventricular synchrony and improved cardiac performance.

Various embodiments of the present disclosure may be used for determination of a pacing timing interval based on comparison between features and/or comparison of time intervals between features of the local and non-local signals. For example, various feature points may be used as reference points in determining a local depolarization (e.g., electrical delay) time in a cardiac cycle between various heart chambers.

As such, a local electrical delay (e.g., delay interval) may be measured, as described herein, as a time interval between right atrium (RA) and right ventricle (RV) activation (e.g., a RA-RV delay interval), a time interval between left atrium (LA) activation and left ventricle (LV) activation (e.g., a LA-LV delay interval), and/or contralateral activation combinations of the atria and ventricles. These activations may be determined by appropriate local placement of electrodes in order to be electrically coupled to (e.g., by being in physical contact with or adjacent to) the one or more atria and/or ventricles. For example, the RA or LA activation can be measured in a locally acquired electrogram from an onset of a change in slope leading to a first and/or a largest peak (e.g., associated with a P-wave), or from the largest peak, among other possibilities for determining the time interval between activation the RA or the LA and activation of the RV or the LV, as described below.

As described herein, the activation of the RA and/or the LA may be determined from intrinsic activation or paced activation. The AV delay for a ventricular pulse (e.g., of the RV and/or the LV) may be determined relative to an intrinsic RA-RV delay interval, an intrinsic LA-LV delay interval, and/or contralateral activation combinations of the atria and ventricles. Alternatively, the AV delay for the ventricular pulse may be determined relative to such intervals based on pacing of one or more of the atria.

A local electrical delay also may be measured, as described herein, as a time interval between initiation of activation of one or both ventricles, as determined by initiation of a QRS complex (e.g., termed "Q", which is a feature that may be indicated by a notable change in slope in an appropriate region of the cardiac cycle determined from a surface electrocardiogram (ECG)), and a first RV or a first LV intracardiac (e.g., locally acquired) electrogram peak (e.g., where the electrogram peak has a positive or negative amplitude at least fifty percent of the largest amplitude positive or negative peak). The first LV intracardiac electrogram peak may be measured by local placement of an electrode so as to be electrically coupled to (e.g., by being in physical contact with or adjacent to) the LV and the first RV intracardiac electrogram peak may be measured by local placement of an electrode so as to be electrically coupled to (e.g., within or adjacent to) the RV.

The first LV intracardiac electrogram peak may be indicative of local depolarization at the LV electrode site and the first RV intracardiac electrogram peak may be indicative of local depolarization at the RV electrode site. The time interval between the initiation of the QRS complex (e.g., at Q) and the first LV intracardiac electrogram peak may be termed a QLV delay interval and the time interval between the initiation of the QRS complex (e.g., at Q) and the first RV intracardiac electrogram peak may be termed a QRV delay interval. Alternative time interval measurements may be between the initiation of the QRS complex and an onset of a change in slope leading to the first RV intracardiac electrogram peak or an onset of a change in slope leading to the first LV intracardiac electrogram peak, and between the initiation of the QRS complex and a largest peak of the RV intracardiac electrogram or the largest peak of the LV electrogram, among other possibilities for determining the time interval between initiation of activation of one or both ventricles and activation of the RV or the LV.

A local electrical delay also may be measured, as described herein, as a time interval between activation of the RV and the LV. In various embodiments, such an interval (e.g., a RV-LV delay interval) can be determined as a time interval between a first RV intracardiac electrogram peak (e.g., where electrogram peak has a positive or negative amplitude at least fifty percent of the largest amplitude positive or negative peak) and a LV intracardiac electrogram peak (e.g., where electrogram peak has a positive or negative amplitude at least fifty percent of the largest amplitude positive or negative peak). Alternative time interval measurements may be between an onset of a change in slope leading to the first RV intracardiac electrogram peak and an onset of a change in slope leading to the first LV intracardiac electrogram peak, and between a largest peak of the RV intracardiac electrogram and the largest peak of the LV electrogram, among other possibilities for determining the time interval between activation of the RV and the LV.

Accordingly, among the various embodiments described in the present disclosure, an implantable cardiac rhythm management (CRM) device may include a plurality of body-implantable electrodes configured to electrically couple to a heart, the plurality of implantable electrodes including at least a first pair of electrodes and a second pair of electrodes. The CRM device may include sense circuitry coupled to the first and second electrode pairs that is configured to sense at least one local cardiac signal via the at least the first pair of electrodes and a non-local cardiac signal via the second electrode pair. The CRM device may include detection circuitry configured to detect a feature of the local signal associated with activation of at least one heart chamber (e.g., at least one of the atrial and/or the ventricular heart chambers) and to detect a feature of the non-local signal associated with activation of at least one ventricular heart chamber. The CRM device also may include a control processor configured to time delivery of one or more pacing pulses (e.g., to the RV and/or the LV) based on a temporal relationship between timing of the local signal feature and timing of the non-local signal feature.

In some embodiments, the CRM device may include a pulse generator disposed in a body-implantable housing of the CRM device. In various embodiments, the CRM device may include the plurality of implantable electrodes configured to electrically couple to the heart being coupled to a housing and at least the first pair of the plurality of electrodes configured to sense the at least one local cardiac signal predominantly indicating cardiac electrical activity within the at least one heart chamber (e.g., at least one of the atrial and/or the ventricular heart chambers) and at least the second pair of the plurality of electrodes configured to sense the non-local cardiac signal, the non-local signal including a superposition of cardiac electrical signals occurring within at least one ventricular heart chamber and associated with a cardiac contraction.

The CRM device may be configured to operate on a beat-by-beat basis, such that the control processor is configured to deliver a given one of the one or more pacing pulses during a next cardiac beat after a cardiac beat in which the sense circuitry senses the local cardiac signal and the non-local cardiac signal. In some embodiments, the control processor may deliver the given one of the one or more pacing pulses in the next cardiac beat after a single cardiac beat in which the timing of the pacing pulse is determined, as described herein. In some embodiments, the control processor may deliver the given one of the one or more pacing pulses in the next cardiac beat after a plurality of cardiac beats in which the timing of the pacing pulse is determined (e.g., after statistical manipulation, such as averaging, etc., of measurements, calculated pulse timings, etc.).

In some embodiments, the local signal feature may include a delay interval, as described herein, between the activation of the at least one heart chamber and a ventricle intracardiac electrogram peak and the non-local signal feature that may include a non-local QRS interval. By way of example, the delay interval may be a QLV delay interval, as described herein, between initiation of the activation (e.g., at Q) of the at least one heart chamber (e.g., at least one of the ventricular heart chambers) and a first LV intracardiac electrogram peak (e.g., that has a positive or negative amplitude at least fifty percent of the largest amplitude positive or negative peak). With regard to the QLV delay interval, the local signal feature may be sensed by the at least the first pair of the electrodes configured to sense the initiation of the activation of the at least one ventricular heart chamber from the non-local site (e.g., the surface ECG) and to sense the first LV intracardiac electrogram peak from a local ventricular site, the detection circuitry configured to detect the local signal feature may be configured to detect the QLV delay interval, and the detection circuitry configured to detect the non-local signal feature may be configured to detect the QRS interval.

In some embodiments, the control processor may be configured to determine an atrioventricular delay to time delivery of one or more atrioventricular pacing pulses (e.g., to the RV and/or to the LV) based on the temporal relationship as determined by a timing of the ventricle intracardiac electrogram peak (e.g., the first LV intracardiac electrogram peak of the QLV delay interval) relative to a time progression through of the non-local QRS interval. For example, the timing of the position of the electrogram peak can be compared to a timing of features in the QRS complex during progression though the QRS interval, the timing of the position of the electrogram peak can be determined as a fraction of the time length of the QRS interval, or the atrioventricular delay to time delivery of the one or more atrioventricular pacing pulses may be determined by a ratio of a time length of the delay interval and a time length of the non-local QRS interval compared to a number of thresholds, among other possibilities for determining the temporal relationship.

By way of example, a ratio value may be calculated with regard to the QLV delay interval by dividing the time length of the QLV delay interval by the time length of the QRS interval. In some examples, the ratio value may be multiplied by 100 to yield a percentage ranging from 1-100%. The ratio value or the percentage may be compared to a number of thresholds to determine adjustment of a time length of the atrioventricular delay relative to at least one of intrinsic RA-RV, RA-LV, LA-LV, and LA-RV delay intervals if the atrioventricular delay is timed with an atrial sense event or at least one of the RA-RV, RA-LV, LA-LV, and LA-RV delay intervals determined from atrial pacing and ventricular sensing when the atrioventricular delay is timed with an atrial pace event. For example, a percentage of less than 60% may indicate that a longer atrioventricular delay will be programmed, whereas a percentage of 60% and greater may indicate that a shorter atrioventricular delay will be programmed. Actual millisecond values for shortening and lengthening the atrioventricular delay relative to a particular number of, and values for, thresholds may be determined statistically, experimentally, and/or based on clinical practice.

Among the various embodiments described in the present disclosure, an implantable CRM system for delivery of pacing therapy may include a pulse generator disposed in a body-implantable housing. The CRM system may include at least a first pair of body-implantable electrodes electrically coupled to the housing and configured to sense at least one local cardiac signal predominantly indicating cardiac depolarization activity close to a local site within at least one heart chamber (e.g., at least one of the atrial and/or the ventricular heart chambers) and a second pair of body-implantable electrodes electrically coupled to the housing and configured to sense a non-local cardiac signal comprising a superposition of cardiac electrical signals occurring within ventricular heart chambers and associated with ventricular depolarizations.

The CRM system also may include a control processor. The control processor may be configured to detect at least one delay interval from the at least one local signal related to depolarization of the at least one heart chamber. The at least one delay interval may be selected from a QRV delay interval, a QLV delay interval, a RA-LV delay interval, a LA-LV delay interval, and/or a RV-LV delay interval. The control processor may be configured to detect a QRS interval from the non-local signal related to depolarization of the ventricular heart chambers. The control processor also may be configured to time delivery of one or more atrioventricular pacing pulses based on a temporal relationship between the at least one delay interval and the QRS interval.

In various embodiments, the control processor may be configured to determine an atrioventricular delay (e.g., for pulsing the RV and/or the LV) based on the temporal relationship, as described herein. In some embodiments, the control processor may be configured to trigger the one or more atrioventricular pacing pulses based on the temporal relationship between a QRV delay interval and the QRS interval or the QLV delay interval and the QRS interval. In some embodiments, the control processor may be configured to compare timing of a RV intracardiac electrogram peak in the QRV delay interval with progression through the QRS interval or timing of a LV intracardiac electrogram peak in the QLV delay interval with progression through the QRS interval. In some embodiments, the control processor may be configured to program a longer atrioventricular delay based on a detection of the RV intracardiac electrogram peak or the LV intracardiac electrogram peak earlier in the progression through the QRS interval than when the detection of the RV or the LV intracardiac electrogram peak is later in the progression through the QRS interval.

Among the various embodiments described in the present disclosure, delivery of pacing therapy may include sensing, using body-implantable electrodes, at least one local cardiac electrical signal and at least one non-local cardiac electrical signal, as described herein. At least one delay interval may be sensed from the at least one local cardiac signal corresponding to depolarization of at least one chamber of a heart (e.g., at least one of the atrial and/or the ventricular heart chambers). In various embodiments, the at least one delay interval can be selected from a QRV delay interval, a QLV delay interval, a RA-LV delay interval, a LA-LV delay interval, and/or a RV-LV delay interval, as described herein. A QRS interval may be sensed from the non-local signal corresponding to depolarization of both ventricular chambers. Timing of delivery of one or more atrioventricular pacing pulses may be based on a temporal relationship between the at least one delay interval sensed from the local signal and the QRS interval sensed from the non-local signal.

In various embodiments, the timing of the delivery of the one or more atrioventricular pacing pulses may include determining an atrioventricular delay based on the temporal relationship between the at least one delay interval and the QRS interval. Determining of the atrioventricular delay based on the temporal relationship may include the temporal relationship being selected from determining a timing of a RV intracardiac electrogram peak (e.g., in the RA-RV, QRV, or RV-LV delay intervals) or a LV intracardiac electrogram peak (e.g., in the LA-LV, QLV, or RV-LV delay intervals) in the at least one delay interval relative to a time progression through the non-local QRS delay interval.

In various embodiments, a ratio may be determined of a time length of the at least one delay interval and a time length of the non-local QRS interval compared to a number of thresholds. Among a number of examples, a QRV delay interval may be derived from a difference between a RA-RV delay interval and a RA-Q delay interval and then divided by the QRS delay interval to provide a first ratio, a QLV delay interval may be derived from a difference between a LA-LV delay interval and a LA-Q delay interval and then divided by the QRS interval to provide a second ratio, a QRV delay interval may be divided by the QRS interval to provide a third ratio, a QLV delay interval may be divided by the QRS interval to provide a fourth ratio, and a difference between a RV or LV to Q delay interval and a RV-LV delay interval and then divided by the QRS interval may be used to provide a fifth ratio, in addition to other examples of using the delay intervals to determine ratios relative to the QRS interval. As previously described, the ratio values, or the percentages derived therefrom, may be compared to a number of thresholds to determine adjustment of a time length of the atrioventricular delay relative to the intrinsic or the pulsed RA-RV delay or LA-LV delay.

In various embodiments, sensing the at least one local cardiac signal may include sensing from at least one of a local RA site, a local LA site, a local RV site, and a local LV site. In some embodiments, the sensing, using the body-implantable electrodes, may include using at least one local cardiac electrical signal predominantly indicating depolarization of the RV chamber and/or the LV chamber and at least one non-local cardiac electrical signal comprising a superposition of cardiac electrical signals occurring within both ventricular chambers and associated with ventricular depolarization. Sensing the delay interval (e.g., the QRV delay interval and/or the QLV delay interval) may include comparing an intracardiac electrogram local signal with a surface electrocardiogram non-local signal (e.g., that determines initiation of a QRS complex at Q). Sensing for the QRS interval may include sensing for a progression of both ventricular chambers through the QRS interval at a site distal from the local site (e.g., distal from the local RV or local LV sites).

Accordingly, the timing of the delivery of the one or more atrioventricular pacing pulses may be used for triggering the atrioventricular pacing based on the temporal relationship between the at least one delay interval and the QRS interval. The timing of the pulsing may be carried out on a beat-by-beat basis, such that the sensing for the delay interval from the at least one cardiac local cardiac signal, the sensing for the QRS interval from the non-local signal, and a timing of delivery of a given one of the one or more atrioventricular pacing pulses are all associated with a single cardiac beat. In some embodiments, timing of the pulsing may be determined based on a plurality of cardiac beats (e.g., after statistical manipulation, such as averaging, etc., of measurements, calculated pulse timings, etc.).

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac rhythm management device, comprising:
a plurality of body-implantable electrodes configured to electrically couple to a heart, the plurality of implantable electrodes including at least a first pair of electrodes and a second pair of electrodes, at least one of the first pair of electrodes to be in direct contact with myocardial tissue for use to sense at least one local cardiac signal close to the contacted myocardial tissue such that a sensed local cardiac signal is representative of an activation signal close to the contacted myocardial tissue, the second pair of electrodes to be not in direct contact with myocardial tissue for use to sense non-local cardiac signals such a sensed non-local cardiac signal effectively provides a superposition of a number of activation signals occurring within the heart;
sense circuitry coupled to the first and second electrode pairs and configured to sense the at least one local cardiac signal via the at least the first pair of electrodes and the non-local cardiac signal via the second electrode pair;
detection circuitry configured to detect a delay interval between an activation of at least one heart chamber and a ventricular intracardiac electrogram peak and to detect a non-local QRS interval; and
a control processor configured to:
determine a temporal relationship between timing of the local signal feature and timing of the non-local signal feature, wherein the temporal relationship includes a ratio of a time length of the delay interval and a time length of the non-local QRS interval;
determine an atrioventricular delay based on the temporal relationship; and
time delivery of one or more pacing pulses based on the temporal relationship and the atrioventricular delay.

2. The device of claim 1, comprising a pulse generator disposed in a body-implantable housing.

3. The device of claim 1, comprising the plurality of implantable electrodes configured to electrically couple to the heart being coupled to a housing and, at least the first pair of the plurality of electrodes configured to sense the at least one local cardiac signal predominantly indicating cardiac electrical activity within the at least one heart chamber and at least the second pair of the plurality of electrodes configured to sense the non-local cardiac signal comprising a superposition of cardiac electrical signals occurring within at least one ventricular heart chamber and associated with a cardiac contraction.

4. The device of claim 1, wherein the device is configured to operate on a beat-by-beat basis.

5. The device of claim 1, wherein the delay interval between an activation of at least one heart chamber and a ventricular intracardiac electrogram peak is a QLV interval.

6. An implantable cardiac rhythm management device, comprising:
a plurality of body-implantable electrodes configured to electrically couple to a heart, the plurality of implantable electrodes including at least a first pair of electrodes and a second pair of electrodes, at least one of the first pair of electrodes to be in direct contact with myocardial tissue for use to sense at least one local cardiac signal close to the contacted myocardial tissue such that a sensed local cardiac signal is representative of an activation signal close to the contacted myocardial tissue, the second pair of electrodes to be not in direct contact with myocardial tissue for use to sense non-local cardiac signals such a sensed non-local cardiac signal effectively provides a superposition of a number of activation signals occurring within the heart;
sense circuitry coupled to the first and second electrode pairs and configured to sense the at least one local cardiac signal via the at least the first pair of electrodes and the non-local cardiac signal via the second electrode pair;
detection circuitry configured to detect a delay interval between an activation of at least one heart chamber and a ventricular intracardiac electrogram peak and to detect a non-local QRS interval;
a pulse generator configured to deliver pacing pulses to myocardial tissue using a least some of the plurality of body-implantable electrodes; and
a control processor configured to:
determine a temporal relationship between timing of the local signal feature and timing of the non-local signal feature, wherein the temporal relationship includes a ratio of a time length of the delay interval and a time length of the non-local QRS interval;

determine an atrioventricular delay based on the temporal relationship;

and time delivery of one or more pacing pulses based on the temporal relationship and the atrioventricular delay.

7. The device of claim 6, comprising the plurality of implantable electrodes configured to electrically couple to the heart being coupled to a housing and, at least the first pair of the plurality of electrodes configured to sense the at least one local cardiac signal predominantly indicating cardiac electrical activity within the at least one heart chamber and at least the second pair of the plurality of electrodes configured to sense the non-local cardiac signal comprising a superposition of cardiac electrical signals occurring within at least one ventricular heart chamber and associated with a cardiac contraction.

8. The device of claim 6, wherein the device is configured to operate on a beat-by-beat basis, such that the control processor is configured to deliver a given one of the one or more pacing pulses during a next cardiac beat after a cardiac beat in which the sense circuitry senses the local cardiac signal and the non-local cardiac signal.

9. The device of claim 6, wherein the delay interval between an activation of at least one heart chamber and a ventricular intracardiac electrogram peak is a QLV interval.

\* \* \* \* \*